(12) United States Patent
Kimchy et al.

(10) Patent No.: US 9,943,273 B2
(45) Date of Patent: Apr. 17, 2018

(54) RADIATION SOURCE FOR INTRA-LUMEN IMAGING CAPSULE

(71) Applicant: CHECK-CAP LTD., Isfiya (IL)

(72) Inventors: Yoav Kimchy, Haifa (IL); Salah Hasoon, Shefar-am (IL)

(73) Assignee: CHECK-CAP LTD., Isfiya (IL)

( * ) Notice: Subject to any disclaimer, the term of this patent is extended or adjusted under 35 U.S.C. 154(b) by 0 days.

(21) Appl. No.: 15/110,946

(22) PCT Filed: Apr. 8, 2014

(86) PCT No.: PCT/IL2014/050340
§ 371 (c)(1),
(2) Date: Jul. 12, 2016

(87) PCT Pub. No.: WO2015/118520
PCT Pub. Date: Aug. 13, 2015

(65) Prior Publication Data
US 2016/0324492 A1    Nov. 10, 2016

Related U.S. Application Data

(60) Provisional application No. 61/935,859, filed on Feb. 5, 2014.

(51) Int. Cl.
*A61B 6/00* (2006.01)
*A61K 51/12* (2006.01)
*A61B 1/04* (2006.01)

(52) U.S. Cl.
CPC .............. *A61B 6/425* (2013.01); *A61B 1/041* (2013.01); *A61B 6/4057* (2013.01); *A61K 51/1262* (2013.01)

(58) Field of Classification Search
CPC ............ A61K 51/12; A61B 6/00; A61B 6/425
See application file for complete search history.

(56) References Cited

U.S. PATENT DOCUMENTS

| | | | | |
|---|---|---|---|---|
| 5,163,896 | A | * 11/1992 | Suthanthiran | A61K 51/1282 600/8 |
| 2003/0153801 | A1 | * 8/2003 | Keller | A61K 31/00 600/3 |
| 2004/0076579 | A1 | * 4/2004 | Coniglione | A61K 51/1282 424/1.11 |
| 2007/0161885 | A1 | * 7/2007 | Kimchy | A61B 5/073 600/407 |
| 2010/0178244 | A1 | | 7/2010 | Arnsdorf et al. |
| 2013/0009120 | A1 | * 1/2013 | Munro, III | G21G 4/06 252/625 |

* cited by examiner

*Primary Examiner* — Michael G Hartley
*Assistant Examiner* — Jagadishwar R Samala
(74) *Attorney, Agent, or Firm* — Soroker Agmon Nordman

(57) ABSTRACT

A method of preparing a radioactive material to serve as a radiation source for an intra-lumen imaging capsule, including, receiving a radioactive substance having grains in powder form, forming a solid pellet wherein the grains of the radioactive substance are dispersed homogenously in the pellet and surrounded by less dense materials having lower radiation absorption.

9 Claims, 3 Drawing Sheets

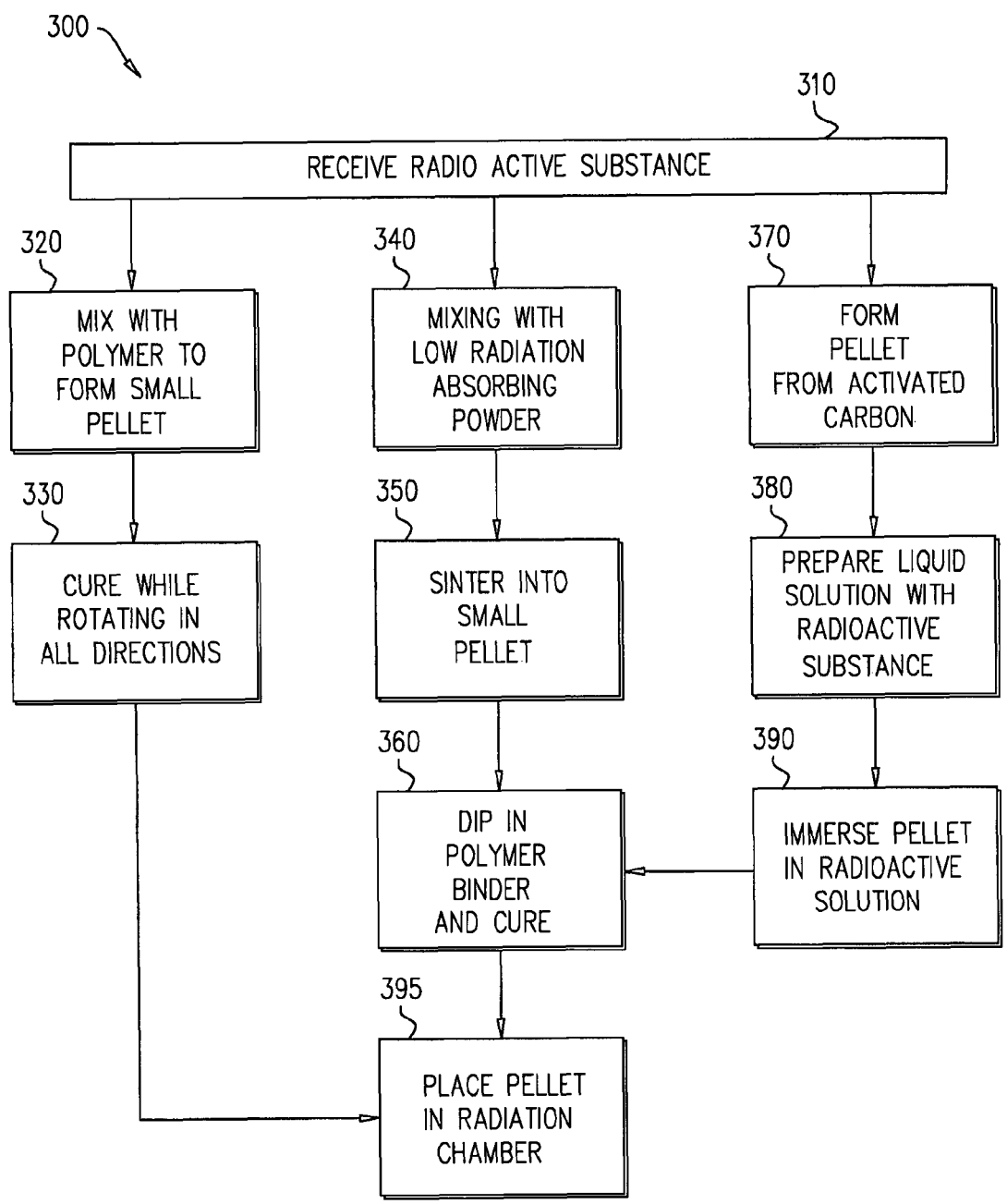

RADIATION SOURCE FOR INTRA-LUMEN IMAGING CAPSULE

RELATED APPLICATIONS

The present application claims priority from U.S. Provisional application No. 61/935,859 filed on Feb. 5, 2014 the disclosure of which is incorporated herein by reference.

TECHNICAL FIELD

The present disclosure relates generally to investigating the insides of a patient using an intra-lumen imaging capsule and more specifically to the radiation source for performing the investigation.

BACKGROUND

One method for examining the gastrointestinal tract for the existence of polyps and other clinically relevant features that may provide an indication regarding the potential of cancer is performed by swallowing an imaging capsule that will travel through the gastrointestinal (GI) tract and viewing the patient's situation internally. In a typical case the trip can take between 24-48 hours, after which the imaging capsule exits in the patient's feces. Generally the capsule will be surrounded by non-transparent liquids therefore a radioactive material is used to image the patient and not a visible light source.

Typically the patient swallows a contrast agent to enhance the imaging ability of the imaging capsule. Then the patient swallows the imaging capsule to examine the gastrointestinal tract while flowing through the contrast agent. The imaging capsule typically includes a radiation source, for example including a radioisotope that emits X-rays or Gamma rays. The radiation is typically collimated to allow it to be controllably directed in a specific direction during the imaging process. In some cases the imaging capsule is designed to measure Compton back-scattering and/or X-ray florescence and wirelessly transmit the measurements (e.g. a count rate) to an external analysis device, for example a computer or other dedicated instruments.

In a typical implementation a radio-opaque contrast agent is used so that a position with a polyp will have less contrast agent and will measure a larger back-scattering count to enhance accuracy of the measurements. Alternatively, other methods may be used to image the gastrointestinal tract.

U.S. Pat. No. 7,787,926 to Kimchy, the disclosure of which is incorporated herein by reference, describes details related to the manufacture and use of such an imaging capsule.

The radiation source used in the imaging capsule should preferably have a long half-life so that it does not need to be used immediately after preparation, rather there would be sufficient time to ship a few imaging capsules to a clinic and have them applied without urgency, for example within a few days before they expire.

Generally a selected amount of radioactive material is placed in a radiation chamber in the imaging capsule. However since the radioactive material is generally a dense molecule it interferes with itself and blocks a large portion of the radiation from being emitted from the imaging capsule. Therefore it is desirable to have the radioactive material arranged differently in the radiation chamber to enhance the emission of radiation.

SUMMARY

An aspect of an embodiment of the disclosure relates to a system and method for preparing a radiation source for an intra-lumen imaging capsule. The method includes preparing or receiving a radioactive substance that includes one or more isotopes of a specific atomic number of which at least one isotope is radioactive and optionally, having a half life greater than 48 hours. The radioactive substance is received as grains in a powder form and is used to prepare a solid pellet in which the grains of the radioactive substance are dispersed homogenously in the pellet and surrounded by less dense materials having lower radiation absorption, so that the radiation emitted from the radioactive grains will not be hindered by other radioactive or non-radioactive grains that have heavy molecules, for example other grains of the radioactive substance from non-radioactive isotopes.

In an exemplary embodiment of the disclosure, the pellet is formed by mixing the radioactive substance with a polymer binder such as epoxy EPO-TEK 301 to form a solid pellet. The mixture is then cured while rotating it so that the heavy grains of the radioactive substance don't settle to one side and ruin the homogeneous dispersion in the pellet.

In an exemplary embodiment of the disclosure, the pellet is formed by mixing the radioactive substance with a low radiation absorbing powder, for example aluminum. The mixture is sintered to form a solid pellet and then dipped in a polymer binder such as an epoxy adhesive to form a protective film around the pellet. The pellet is cured so that the coating film will prevent the pellet from crumbling.

In an exemplary embodiment of the disclosure, the pellet is formed from activated carbon, which has a high degree of micro porosity. The radioactive substance is used to form a liquid solution and the pellet is immersed in the solution to absorb molecules/atoms from the solution of the radioactive substance. After immersing the pellet it is dipped in a polymer binder such as an epoxy adhesive to form a protective film around it. The pellet is cured so that the coating film will prevent the pellet from crumbling. Optionally, other methods may be used to form the solid pellet.

There is thus provided according to an exemplary embodiment of the disclosure, a method of preparing a radioactive material to serve as a radiation source for an intra-lumen imaging capsule, comprising:

receiving a radioactive substance having grains in powder form;

forming a solid pellet wherein the grains of the radioactive substance are dispersed homogenously in the pellet and surrounded by less dense materials having lower radiation absorption.

In an exemplary embodiment of the disclosure, the forming comprises:

mixing the radioactive substance with a polymer binder to form the solid pellet; and curing the mixture while rotating it so that the grains of the radioactive substance don't settle and ruin the homogenous dispersion.

Alternatively, the forming comprises:

mixing the radioactive substance with a low radiation absorbing powder;

sintering the mixture to form the pellet;

dipping the pellet in a polymer binder; and curing the pellet.

Further alternatively, the forming comprises:

molding the pellet from activated carbon;

preparing a liquid solution from the radioactive substance;

immersing the pellet in the liquid solution to absorb grains of the radioactive substance;

dipping the pellet in a polymer binder; and curing the pellet.

In an exemplary embodiment of the disclosure, the radioactive substance includes an isotope with a half life greater than 48 hours. Optionally, the radioactive substance includes the isotope Os191. In an exemplary embodiment of the disclosure, the radioactive substance is prepared by separating it from molecules with different atomic numbers by a chemical separation process. Alternatively or additionally, the radioactive substance is prepared by separating it from molecules with different mass numbers by an isotope separation process.

In an exemplary embodiment of the disclosure, the radioactive substance includes an isotope selected from the group consisting of W181, Hg197, Tl201 and Pt195m. Optionally, the radioactive substance includes multiple isotopes having a specific atomic number of which at least one is radioactive with a half life greater than 48 hours.

There is further provided according to an exemplary embodiment of the disclosure, a radioactive material for providing radiation by an intra-lumen imaging capsule, comprising:

a radioactive substance having grains in powder form;

a solid pellet wherein the grains of the radioactive substance are dispersed homogenously in the pellet and surrounded by less dense materials having lower radiation absorption.

In an exemplary embodiment of the disclosure, the less dense materials having lower radiation absorption include a polymer binder. Optionally, the less dense materials having lower radiation absorption include a low radiation absorbing powder; and wherein the pellet is coated with a cured polymer binder. In an exemplary embodiment of the disclosure, the pellet includes a mold of activated carbon that was dipped in a liquid solution of the radioactive substance; and wherein the pellet is coated with a cured polymer binder. Optionally, the radioactive substance includes an isotope with a half life greater than 48 hours. In an exemplary embodiment of the disclosure, the radioactive substance includes the isotope Os191.

BRIEF DESCRIPTION OF THE DRAWINGS

The present disclosure will be understood and better appreciated from the following detailed description taken in conjunction with the drawings. Identical structures, elements or parts, which appear in more than one figure, are generally labeled with the same or similar number in all the figures in which they appear, wherein:

FIG. 3 is a flow diagram of a method of preparing a radioactive substance for use as a radiation source in an imaging capsule, according to an exemplary embodiment of the disclosure.

DETAILED DESCRIPTION

Figure 1:
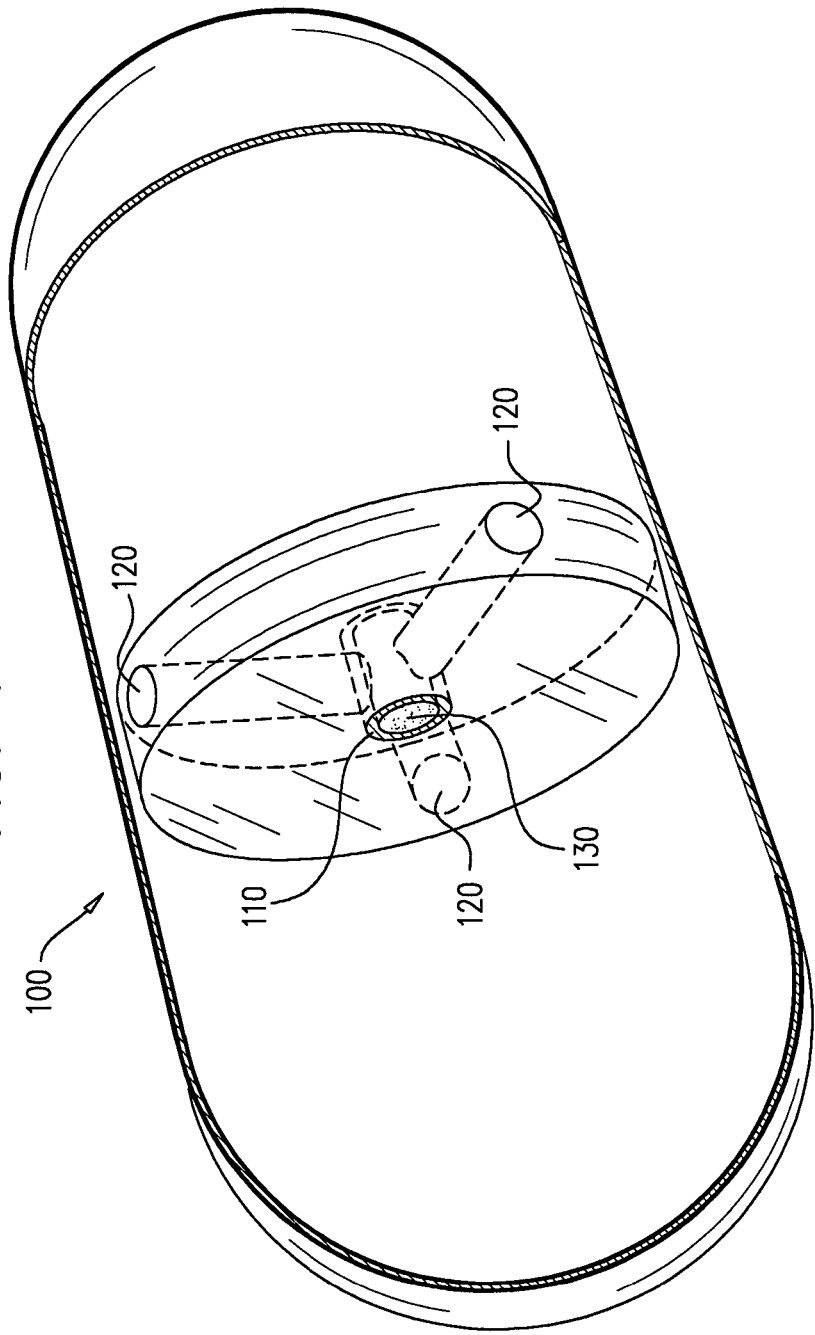
FIG. 1 is a schematic illustration of an imaging capsule with a radioactive material, according to an exemplary embodiment of the disclosure.

FIG. 1 is a schematic illustration of an imaging capsule 100 with a radioactive material 130. In an exemplary embodiment of the disclosure, the imaging capsule includes a radiation chamber 110 for placing the radioactive material 130. Optionally, radiation chamber 110 is designed with openings having collimators 120 extending therefrom so that the radiation will be emitted through the collimators to image the surroundings of imaging capsule 100.

In an exemplary embodiment of the disclosure, the radiation material 130 is composed from a radioisotope such as Os191, W181, Hg197, Tl201, Pt195m or other radioisotopes with a half life time of at least 2-3 days and having specific activity strong enough to image inside the user. In an exemplary embodiment of the disclosure, the radioisotope is processed as described below so that small amounts of the radioisotope will be surrounded by light material that will maximize efficiency by reducing blocking emission of X-rays and Gama-rays from the radioactive material. In contrast using a radiation material 130 with a highly concentrated radioisotope consistency is less cost efficient since a lot of the radiation will be blocked by the material itself.

Figure 2:
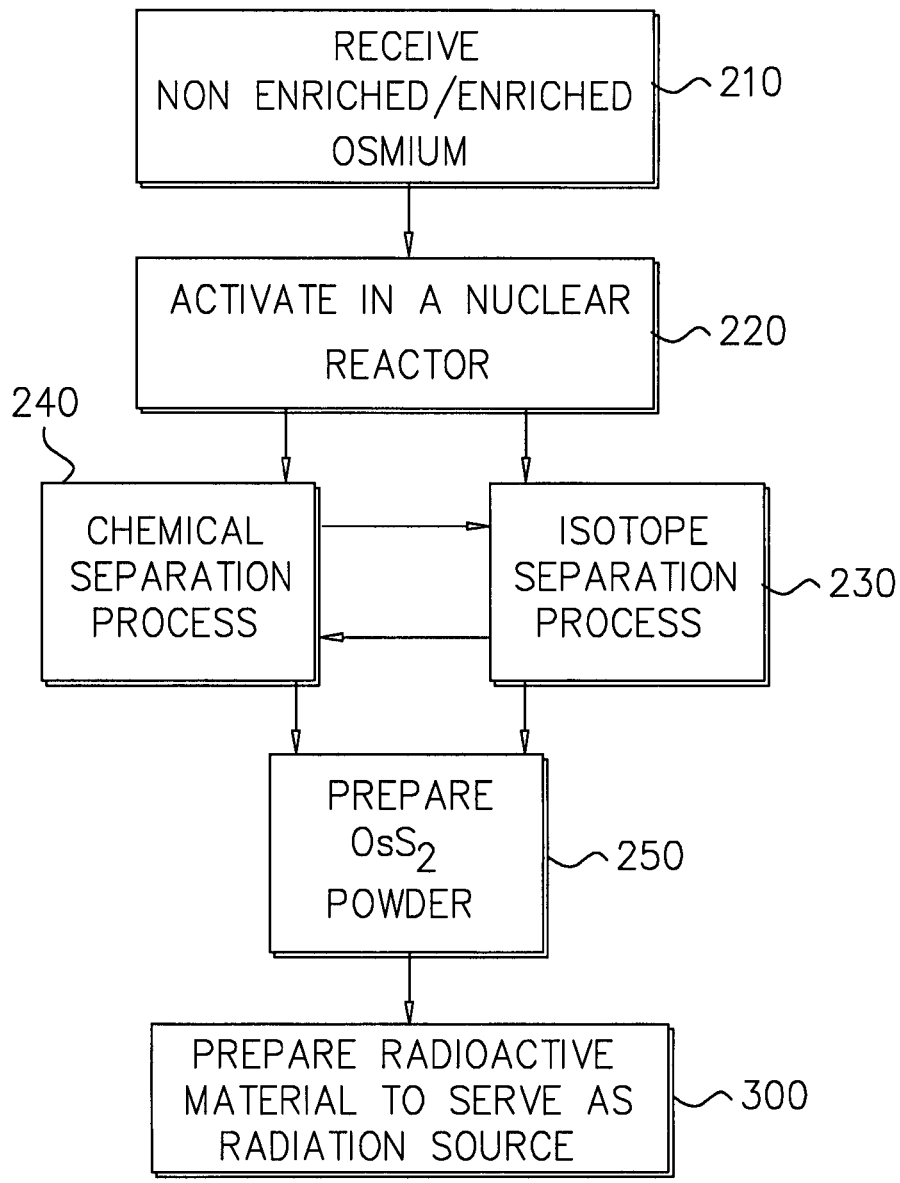
FIG. 2 is a flow diagram of a method of preparing a radioactive substance, according to an exemplary embodiment of the disclosure.

In some embodiments of the disclosure, Osmium 191 (Os191) is used as the radioisotope for preparing a radioactive substance (e.g. in powder form) that will be used to form radioactive material 130 for use in imaging capsule 100. Os 191 has a half life of about 15.4 days making it attractive for use in radioactive material 130. FIG. 2 is a flow diagram of a method 200 of preparing the radioactive substance (e.g. $OsS_2$ powder from enriched or non-enriched Osmium), according to an exemplary embodiment of the disclosure.

In an exemplary embodiment of the disclosure, enriched Osmium 190 (e.g. 92% or more enriched) is received (210) for preparing the radioactive substance. Optionally, the enriched Osmium is activated (220) in a nuclear reactor, for example by bombarding the Os190 with an appropriate thermal neutron flux, for example of the order of $1E14$ n/cm$^2$ per second to $5E15$ n/cm$^2$ per second. Optionally, the activation is performed for a period of a few hours to a few hundred hours to prepare a sufficient amount of radioactive material Os191 with sufficient specific activity, for example between 10 mCi/mg to 100 mCi/mg.

In an exemplary embodiment of the disclosure, the results from the activation process include Osmium 190 (non activated), Osmium 191 and Iridium 192. Optionally, a chemical process is applied (240) to form a powder based on the Osmium molecules (of all isotopes e.g. 190, 191) and to discard the Iridium. Alternatively or additionally, an isotope separation process (230) is applied to the results of the activation process, separating between all the isotopes including between Iridium and Osmium. In some embodiments of the disclosure, the isotope separation process is applied first and renders the chemical process superfluous.

In some embodiments of the disclosure, the chemical process is applied first. Optionally, the chemical process (240) includes heating the radioactive mixture resulting from the activation process, provided as a powder, to about 200 degrees centigrade or higher in air to release an $OsO_4$ gas. Alternatively, the mixture is mixed with concentrated $HNO_3$ or $H_2SO_4$ and heated to release the $OsO_4$ gas.

Further alternatively, one part Osmium powder is fused with four parts $KNO_3$ and four parts KOH at 350 to 500 degrees centigrade and dissolved in water to give $K_2[OsO_4(OH)_2]$ in an aqueous solution (with some Iridium radioisotope (Ir192) impurity in the solution). Optionally, $HNO_3$ or $H_2SO_4$ is added to neutralize the solution. The solution is heated to 50-60 degrees centigrade and $OsO_4$ is released in the process by passing an inert gas such as Argon in the solution.

In an exemplary embodiment of the disclosure, an OsS2 powder is then prepared (250) by having the $OsO_4$ gas cold trapped in a KOH solution forming $K_2[OsO_4(OH)_2]$, which now has no Iridium impurities. Optionally, by adding NaHS, $OsS_2$ precipitate can be separated and dried. In an exemplary embodiment of the disclosure, the resulting $OsS_2$ powder is used as the radioisotope for production of the radioactive material 130 to be placed in radiation chamber 110 of imaging capsule 100.

In some embodiments of the disclosure, the isotope separation process (230) is applied to separate between Os191 and Os190 when it is in gas form as $OsO_4$ before being trapped by the KOH solution. Optionally, the isotope separation process (230) can be by laser isotope separation, electromagnetic isotope separation diffusion isotope separation, SILEX isotope separation, centrifugal isotope separation or any other know method of isotope separation. Optionally, when performing isotope separation, $OsF_6$ can be used instead of $OsO_4$.

In an exemplary embodiment of the disclosure, once the Osmium isotopes have been separated the same process (250) for producing $OsS_2$ powder is applied. However the advantage in separating the isotopes is that the $OsS_2$ powder can be selected to be prepared entirely with the enriched Os191 molecules instead of having both Os190 and OS191 wherein the Os191 typically constitutes only a small percent of the Osmium molecules in the $OsS_2$ powder, for example about 0.1-1 percent. Optionally, the specific activity of the isotope separated $OsS_2$ powder is approximately 100-1000 times higher (e.g. 10 mCi/µg to 100 mCi/µg) so that less powder can be used to achieve the same level of radiation. Accordingly, less of radioactive material 130 can be used as the radioactivity is more concentrated, so the size and weight of elements of imaging capsule 100 (e.g. the collimator) can be reduced.

In an exemplary embodiment of the disclosure, non-enriched Osmium can be received (210), for example a mixture of Os188, Os189, Os190 (e.g. about 26% Os190— as in its natural abundance) and all other isotope of Osmium. Optionally, the mixture is activated (220) in a nuclear reactor by bombarding it with an appropriate thermal neutron flux. After activating the mixture the isotopes are separated by a separation process (230) such as laser isotope separation, electromagnetic isotope separation diffusion isotope separation, SILEX isotope separation, centrifugal isotope separation or any other know method of isotope separation. Optionally, the separation process will separate between Os191 from all other Osmium isotopes by transforming it into a gas form such as ° sat or $OsF_6$. Afterwards the radioactive Os191 is trapped by a KOH solution and the process described above is applied to prepare (250) an $OsO_2$ powder from the Os191 molecules. Since Os191 is used, the specific activity of the powder is about 100-1000 times higher (e.g. 10 mCi/µg to 100 mCi/µg) than by preparing the powder from non-separated Os190 and Os191. Accordingly, a few micrograms of $OsO_2$ are sufficient to give the required activity per source.

Accordingly, the initial Osmium molecules received (210) may be non-enriched or enriched. Optionally, preparation of the radioactive substance for use in preparing radioactive material 130 may be by using a chemical separation process (240), an isotope separation process (230) or a combination of both. Optionally, the use of isotope separation process (230) is generally more costly but will provide in the end a radioactive material 130 that is more homogenous and with considerably reduced self absorption relative to a radioactive material 130 prepared by only using a chemical separation process without isotope separation. Optionally, after preparing a radioactive substance (e.g. $OsO_2$ powder) from the received material, a preparation process (300) will be applied to prepare radioactive material 130 having a desired form to serve as the radiation source in imaging capsule 100 from the radioactive substance.

FIG. 3 is a flow diagram of method (300) of preparing radioactive material 130 for use as a radiation source in imaging capsule 100. In some embodiments of the disclosure, other materials can be used to prepare a radioactive substance that can then be converted into the required form to serve as radioactive material 130.

In some embodiments of the disclosure, enriched Tungsten (W180) with e.g. more than about 92% isotopic enrichment is activated in a nuclear reactor. Optionally, the Tungsten is placed in a thermal neutron flux of the order of about 1E14 n/cm² per second to 5E15 n/cm² per second for a period of a few hours to a few hundred hours to achieve sufficient specific activity, for example 10 mCi/mg to 100 mCi/mg of W181. Optionally, the W181 with a half life of about 121 days is provided as a powder that can serve as the radioactive substance for applying preparation process (300) to prepare radioactive material 130.

In some embodiments of the disclosure, enriched Mercury (Hg196) with e.g. more than about 92% isotopic enrichment is activated in a nuclear reactor. Optionally, the Mercury is placed in a thermal neutron flux of the order of about 1E14 n/cm² per second to 5E15 n/cm² per second for a period of a few hours to a few hundred hours to achieve sufficient specific activity, for example 10 mCi/mg to 100 mCi/mg of Hg197. Optionally, the Hg197 with a half life of about 64 hours is provided as a powder that can serve as the radioactive substance for applying preparation process (300) to prepare radioactive material 130.

In some embodiments of the disclosure, Platinum (Pt195m) with specific activity, for example 10 mCi/mg to 100 mCi/mg is produced to serve as the radiation source for imaging capsule 100. Pt195m has a half life of about 4 days. Optionally, the Pt195 is provided as a powder to serve as the radioactive substance for applying preparation process (300) to prepare radioactive material 130.

In some embodiments of the disclosure, Thallium (Tl201) with a half life of about 3 days is produced using a cyclotron. Optionally, the Tl201 is provided as a powder to serve as the radioactive substance for applying preparation process (300) to prepare radioactive material 130.

In an exemplary embodiment of the disclosure, the method (300) of preparing one of the radioactive substances described above or other radioactive substances for use as the radioactive material 130 in imaging capsule 100 includes:

1. Receiving the radioactive substance (310) optionally in powder form;
2. Applying one of the following three options to form a solid radiation material with grains of the radioactive substance essentially homogenously dispersed in the resulting solid and wherein the rest of the solid is made up from a less-dense material with lower radiation absorption, so that the radiation emitted by the radioactive grains will flow freely from radioactive material 130:

(I) Mixing (320) the radioactive powder with a binder polymer, for example EPO-TEK 301 that is manufactured by Epoxy Technology INC from Massachusetts U.S.A. Optionally, the mixture is placed in a small container with low absorption of X-ray and Gamma radiation (e.g. a plastic or aluminum container) to form a small pellet. The binder polymer is allowed to cure (330) slowly (e.g. with a low heat source) while keeping the pellet continuously and/or randomly rotating in 3 orthogonal axis to maintain uniform distribution of the heavy radioactive substance powder, so that it won't sink to one side. Optionally, the resulting small pellet serves as radioactive material 130 in imaging capsule 100. The pellet is then placed (395) in radiation chamber 110 to serve as radiation material 130.

(II) Mixing (340) the radioactive powder with a low radiation absorbing powder, for example aluminum powder and/or a ceramic binder. In an exemplary embodiment of the disclosure, the mixture is sintered (350) into a small pellet. Optionally, the small pellet is dipped (360) in a polymer binder such as EPO-TEK 301 or other adhesive material to prevent crumbling of the pellet. The pellet is then cured (e.g. with a low heat source) and placed (395) in radiation chamber 110 to serve as radiation material 130.

(III) Form (370) a pellet from activated carbon. Optionally, prepare (380) a liquid solution from the radioactive substance powder, and then immerse (390) the pellet in the liquid solution, so that the activated carbon absorbs the radioactive material homogeneously in the pellet. Optionally, the pellet is dipped (360) in a polymer binder such as EPO-TEK 301 or other adhesive material to form a film around the pellet and prevent crumbling of the pellet. The pellet is then cured (e.g. with a low heat source) and placed (395) in radiation chamber 110 to serve as radiation material 130.

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the disclosure. Further combinations of the above features are also considered to be within the scope of some embodiments of the disclosure. It will also be appreciated by persons skilled in the art that the present disclosure is not limited to what has been particularly shown and described hereinabove.

We claim:

1. A method of preparing a radioactive material to serve as a radiation source for an intra-lumen imaging capsule, comprising:
   receiving a radioactive substance having grains in powder form;
   forming a solid pellet wherein the grains of the radioactive substance are dispersed homogenously in the pellet and surrounded by less dense materials having lower radiation absorption;
   wherein said forming comprises:
   mixing the radioactive substance with a polymer binder to form the solid pellet; and
   curing the mixture while rotating it so that the grains of the radioactive substance don't settle and ruin the homogenous dispersion.

2. A method of preparing a radioactive material to serve as a radiation source for an intra-lumen imagine capsule, comprising:
   receiving a radioactive substance having grains in powder form;
   forming a solid pellet wherein the grains of the radioactive substance are dispersed homogenously in the pellet and surrounded by less dense materials having lower radiation absorption;
   wherein said forming comprises:
   mixing the radioactive substance with a low radiation absorbing powder;
   sintering the mixture to form the pellet;
   dipping the pellet in a polymer binder; and
   curing the pellet.

3. A method of preparing a radioactive material to serve as a radiation source for an intra-lumen imaging capsule, comprising:
   receiving a radioactive substance having grains in powder form;
   forming a solid pellet wherein the grains of the radioactive substance are dispersed homogenously in the pellet and surrounded by less dense materials having lower radiation absorption;
   wherein said forming comprises:
   molding the pellet from activated carbon;
   preparing a liquid solution from the radioactive substance;
   immersing the pellet in the liquid solution to absorb grains of the radioactive substance;
   dipping the pellet in a polymer binder; and
   curing the pellet.

4. A method according to claim 1, wherein the radioactive substance includes an isotope with a half life greater than 48 hours.

5. A method according to claim 1, wherein the radioactive substance includes the isotope Os191.

6. A method according to claim 1, wherein the radioactive substance is prepared by separating it from molecules with different atomic numbers by a chemical separation process.

7. A method according to claim 1, wherein the radioactive substance is prepared by separating it from molecules with different mass numbers by an isotope separation process.

8. A method according to claim 1, wherein the radioactive substance includes an isotope selected from the group consisting of W181, Hg197, Tl201 and Pt195m.

9. A method according to claim 1, wherein the radioactive substance includes multiple isotopes having a specific atomic number of which at least one is radioactive with a half life greater than 48 hours.

* * * * *